(12) United States Patent
Ferrie et al.

(10) Patent No.: US 12,349,725 B2
(45) Date of Patent: Jul. 8, 2025

(54) SUBSTITUTE SMOKING CONSUMABLE

(71) Applicant: NERUDIA LIMITED, Liverpool (GB)

(72) Inventors: Kate Ferrie, Liverpool (GB); Edward Ross Shenton, Liverpool (GB)

(73) Assignee: IMPERIAL TOBACCO LIMITED, Bristol (GB)

( * ) Notice: Subject to any disclaimer, the term of this patent is extended or adjusted under 35 U.S.C. 154(b) by 592 days.

(21) Appl. No.: 16/946,282

(22) Filed: Jun. 15, 2020

(65) Prior Publication Data

US 2020/0375244 A1     Dec. 3, 2020

Related U.S. Application Data

(63) Continuation of application No. PCT/EP2018/084043, filed on Dec. 7, 2018, and a
(Continued)

(30) Foreign Application Priority Data

Dec. 15, 2017 (GB) ...................................... 1721029
Dec. 15, 2017 (GB) ...................................... 1721032
(Continued)

(51) Int. Cl.
    *A24D 1/20*        (2020.01)
    *A24B 3/14*        (2006.01)
(Continued)

(52) U.S. Cl.
    CPC .................. *A24D 1/20* (2020.01); *A24B 3/14* (2013.01); *A24D 3/17* (2020.01); *A61M 15/06* (2013.01)

(58) Field of Classification Search
None
See application file for complete search history.

(56) References Cited

U.S. PATENT DOCUMENTS

| | | | |
|---|---|---|---|
| 3,258,015 A | 6/1966 | Drummond |
| 3,356,094 A | 12/1967 | Drummond |
| | (Continued) | | |

FOREIGN PATENT DOCUMENTS

| | | |
|---|---|---|
| CN | 2225147 Y | 4/1996 |
| CN | 202750702 U | 2/2013 |
| | (Continued) | |

OTHER PUBLICATIONS

Author and date unknown, Rien Pipe, How much nicotine is in my cigarette?, Onlinehttps://www.sayonarasmoking.com/how-much-nicotine-is-in-one-cigarette/ [Accessed Mar. 2, 2020].
(Continued)

*Primary Examiner* — Katherine A Will
(74) *Attorney, Agent, or Firm* — Perkins Coie LLP; Adeh Vartanian (57) ABSTRACT

A heat not burn consumable (1) is provided. The consumable includes a tubular vapour generating member (7) defining a channel therethrough. At least an active portion of the vapour generating member is configured to be heated by a heater to produce vapour. The tubular vapour generating member has an inlet to the channel at a first end of the consumable, the first end of the consumable being for cooperation with a heating device. The active portion of the vapour generating member has a sidewall which has a thickness greater than 0.1 mm. This allows for rapid and consistent heating of the vapour generating member. The active portion comprises an amount of an active substance which is between 0.0001 milligrams per mm^2 and 0.02 milligrams per mm^2 of said internal surface area. The vapour generating member has an overall length which is greater than 50% of a total length of the consumable. This may allow for efficient manufacture of the consumable. The consumable also includes an inactive structural tube in axial
(Continued)

abutment with the tubular vapour generating member and located downstream of the vapour generating member. A wrapper overwraps the vapour generating member and at least a portion of the inactive tube. This may allow for efficient manufacture of the consumable.

24 Claims, 8 Drawing Sheets

Related U.S. Application Data continuation of application No. PCT/EP2018/084047, filed on Dec. 7, 2018, and a continuation of application No. PCT/EP2018/084040, filed on Dec. 7, 2018, and a continuation of application No. PCT/EP2018/084046, filed on Dec. 7, 2018.

(30) Foreign Application Priority Data

Dec. 15, 2017 (GB) ..................................... 1721035
Dec. 15, 2017 (GB) ..................................... 1721038

(51) Int. Cl.
*A24D 3/17* (2020.01)
*A61M 15/06* (2006.01)

(56) References Cited

U.S. PATENT DOCUMENTS

| | | | |
|---|---|---|---|
| 4,340,072 A | 7/1982 | Bolt et al. | |
| 4,380,241 A | 4/1983 | Horsewell | |
| 5,060,667 A | 10/1991 | Strubel | |
| 5,388,594 A * | 2/1995 | Counts | A24F 40/485 131/194 |
| 5,839,449 A * | 11/1998 | Banerjee | A24D 3/043 131/342 |
| 9,738,622 B2 | 8/2017 | Dull et al. | |
| 10,506,825 B2 | 12/2019 | Besso et al. | |
| 2002/0134394 A1 | 9/2002 | Baskevitch et al. | |
| 2005/0016549 A1 | 1/2005 | Banerjee et al. | |
| 2007/0169785 A1 | 7/2007 | Gedevanishvili et al. | |
| 2008/0163877 A1 | 7/2008 | Zhuang et al. | |
| 2010/0300467 A1 | 12/2010 | Kuistila et al. | |
| 2011/0192408 A1 | 8/2011 | Inagaki et al. | |
| 2014/0299144 A1 | 10/2014 | Fiebelkorn | |
| 2015/0122277 A1 | 5/2015 | Frobisher et al. | |
| 2019/0045837 A1 | 2/2019 | Spencer | |
| 2020/0008470 A1 * | 1/2020 | Reevell | A24F 40/42 |
| 2020/0205467 A1 * | 7/2020 | Liu | A24B 15/167 |

FOREIGN PATENT DOCUMENTS

| | | | |
|---|---|---|---|
| CN | 103271435 | | 9/2013 |
| CN | 104983070 | | 10/2015 |
| CN | 105768191 | A | 7/2016 |
| CN | 106723382 | | 5/2017 |
| CN | 107173851 | A | 9/2017 |
| DE | 2620274 | A | 11/1977 |
| DE | 4020496 | C8 | 1/1991 |
| EP | 0481192 | C9 | 4/1992 |
| EP | 2076172 | A2 | 7/2009 |
| EP | 3035811 | B1 | 12/2017 |
| GB | 1083761 | | 9/1967 |
| GB | 2201080 | A | 8/1988 |
| GB | 2224921 | | 5/1990 |
| JP | 2010047389 | A | 3/2010 |
| WO | 9607336 | | 3/1996 |
| WO | 2007042941 | A2 | 4/2007 |
| WO | 2013043299 | A2 | 3/2013 |
| WO | 2013098409 | A1 | 7/2013 |
| WO | 2013102609 | A2 | 7/2013 |
| WO | 2015075650 | A1 | 5/2015 |
| WO | 2016023965 | A1 | 2/2016 |

OTHER PUBLICATIONS

Author unknown, Apr. 17, 2019, How much nicotine do HEETS for IQOS contain compared to a standard cigarette, Online, https://www.iqosmag.co.uk/How-much-nicotine-do-HEETS-for-IQOS-contain-compared-to-a-standard-cigarette-A_6540 [Accessed Mar. 2, 2020].
Combined Search and Examination Report Under Sections 17 & 18(3) dated Jun. 14, 2018 for Application No. GB1721029.5, 8 pages.
Combined Search and Examination Report Under Sections 17 & 18(3) dated Jun. 14, 2018 for Application No. GB1721032.9, 9 pages.
Combined Search and Examination Report Under Sections 17 & 18(3) dated Jun. 14, 2018 for Application No. GB1721035.2, 9 pages.
Combined Search and Examination Report Under Sections 17 & 18(3) dated Jun. 14, 2018 for Application No. GB1721038.6, 8 pages.
International Search Report and Written Opinion dated Apr. 2, 2019 for Application No. PCT/EP2018/084040, 9 pages.
International Search Report and Written Opinion dated Apr. 2, 2019 for Application No. PCT/EP2018/084043, 9 pages.
International Search Report and Written Opinion dated Apr. 2, 2019 for Application No. PCT/EP2018/084046, 9 pages.
International Search Report and Written Opinion dated Apr. 2, 2019 for Application No. PCT/EP2018/084047, 9 pages.
https://archive.org/stream/regulationoftoba01unit#page/n0/mode/2up Regulation of Tobacco Products (Part 1), Hearings before the subcommittee on health & the environment of the committee on energy and commerce, Mar. 25 & Apr. 14, 1994, Serial No. 103-149 pp. 72-105 (In particularly pp. 86-88; click see other formats.).
IP Office Japan, Notice of Reasons for Refusal for Application No. 2020-532897, Mail date: Mar. 28, 2023, English machine translation, 7 pages.
IP Office Japan, Notice of Reasons for Refusal for Application No. 2020-532897, Mail date: Nov. 8, 2022, English machine translation, 7 pages.
IP Office Japan, Notice of Reasons for Refusal for Application No. 2020-532898, Mail date: Nov. 8, 2022, English machine translation, 7 pages.
IP Office Japan, Notice of Reasons for Refusal for Application No. 2020-532986, Mail date: Nov. 8, 2022, English machine translation, 6 pages.
IP Office Japan, Notice of Reasons for Refusal for Application No. 2020-532986, Mail date: Mar. 28, 2022, English machine translation, 6 pages.
IP Office Japan, Notice of Reasons for Refusal for Application No. 2020-532987, Mail date: Mar. 28, 2023, English machine translation, 6 pages.
IP Office Japan, Notice of Reasons for Refusal for Application No. 2020-532987, Mail date: Nov. 8, 2022, English machine translation, 6 pages.
EPO, Extended European Search Report; Application No. 24217573.5. Mail Date: Mar. 17, 2025. 7 pages.

* cited by examiner

SUBSTITUTE SMOKING CONSUMABLE

CROSS-REFERENCE TO RELATED APPLICATION(S)

This application is a continuation of International Application No. PCT/EP2018/084040 filed Dec. 7, 2018, which claims the benefit of Great Britain Patent Application No. 1721029.5 filed Dec. 15, 2017; and is a continuation of PCT/EP2018/084043 filed Dec. 7, 2018, which claims the benefit of Great Britain Patent Application No. 1721032.9 filed Dec. 15, 2017; and is a continuation of PCT/EP2018/084046 filed Dec. 7, 2018, which claims the benefit of Great Britain Patent Application No. 1721035.2 filed Dec. 15, 2017; and is a continuation of PCT/EP2018/084047 filed Dec. 7, 2018, which claims the benefit of Great Britain Patent Application No. 1721038.6 filed Dec. 15, 2017, all of which are incorporated herein by reference.

FIELD OF THE INVENTION

The present invention relates to a consumable for a smoking substitute device. In particular, but not exclusively, to a heat not burn consumable comprising tobacco.

BACKGROUND

The "smoking" of tobacco is generally considered to expose a smoker to potentially harmful substances. It is generally thought that a significant amount of the potentially harmful substances are generated through the heat caused by the burning and/or combustion of the tobacco and the constituents of the burnt tobacco in the tobacco smoke itself.

Combustion of organic material such as tobacco is known to produce tar and other potentially harmful by-products. There have been proposed various smoking substitute devices in order to avoid the smoking of tobacco.

Such substitute devices can form part of nicotine replacement therapies aimed at people who wish to stop smoking and overcome a dependence on nicotine.

Substitute devices may comprise electronic systems that permit a user to simulate the act of smoking by producing an aerosol that is drawn into the lungs through the mouth (inhaled) and then exhaled. The inhaled aerosol typically bears nicotine and/or flavourings without, or with fewer of, the odour and health risks associated with traditional smoking.

In general, substitute devices and systems are intended to provide a substitute for the rituals of smoking, whilst providing the user with a similar experience and satisfaction to those experienced with traditional smoking and tobacco products.

The popularity and use of smoking-substitute devices has grown rapidly in the past few years. Although originally marketed as an aid to assist habitual smokers wishing to quit tobacco smoking, consumers are increasingly viewing smoking substitute devices as desirable lifestyle accessories. Some substitute devices are designed to resemble a traditional cigarette and are cylindrical in form with a mouthpiece at one end. Other substitute devices do not generally resemble a cigarette (for example, the substitute device may have a generally box-like form).

There are a number of different categories of substitute systems, each utilising a smoking substitute approach. A substitute approach corresponds to the manner in which the substitute system operates for a user.

An approach for a substitute system is the so-called "heat not burn" (HNB) approach in which tobacco, whether leaf tobacco or reconstituted tobacco, is heated or warmed to release vapour. The vapour may contain nicotine and/or flavour(s). In the HNB approach the intention is that the tobacco is not burned and does not undergo combustion.

In general, an HNB system includes a heating device and consumable. The consumable includes the tobacco material. The consumable is configured for engagement with the heating device. During use, heat is imparted to the tobacco material from a heat source of the heating device. Air flow through the tobacco material causes moisture in the tobacco material to be released as vapour. A first vapour may thus be formed from a carrier in the tobacco material, for example polyglycol (PG) or vegetable glycerine (VG). In addition, volatile compounds may also be released from the tobacco as a second vapour. The vapour(s) released from the tobacco are entrained in the airflow drawn through the tobacco.

As the vapours pass through the device (entrained in the airflow) from an inlet to a mouthpiece (outlet), the vapours cool and condense to form an aerosol for inhalation by the user. The aerosol contains the volatile compounds.

In HNB systems, heating as opposed to burning the tobacco material is believed to cause fewer, or smaller quantities, of the more harmful compounds ordinarily produced during smoking. Consequently, the HNB approach may reduce the odour and/or health risks that can arise through the burning, combustion and pyrolytic degradation of tobacco.

A first existing implementation of the HNB approach is the IQOS™ device from Philip Morris Ltd. The IQOS™ device uses a consumable element, including reconstituted tobacco located in a wrapper. The consumable includes a holder incorporating a mouthpiece. The consumable may be inserted into a heater device. The thermal heater device has a thermally conductive heating knife which penetrates the reconstituted tobacco of the consumable, when the consumable is inserted into the heating device. Activation of the heating device heats the heating element, which, in turn, heats the tobacco in the consumable. The heating of the tobacco causes it to release nicotine vapour and flavours which may be drawn through the mouthpiece by the user through inhalation.

A second existing implementation of the HNB approach is the device known as "Glo"™ from British American Tobacco p.l.c. Glo™ comprises a relatively thin consumable. The consumable includes leaf tobacco which is heated in a heating device. When the consumable is placed in the heating device, the tobacco is surrounded by a heating element. Activation of the heating device heats the heating element, which, in turn, heats the tobacco in the consumable. The heating of the tobacco causes it to release nicotine vapour and flavours which may be drawn through the consumable by the user through inhalation. The tobacco, when heated by the heating device, is configured to produce vapour when heated rather than when burned (as in a smoking apparatus, e.g. a cigarette). The tobacco may contain high levels of aerosol formers (carrier), such as vegetable glycerine ("VG") or propylene glycol ("PG").

Common to both the IQOS™ and Glo™ devices is uneven and incomplete heating of the tobacco, or possible burning of some regions of the tobacco.

Aspects and embodiments of the invention were devised with the foregoing in mind.

SUMMARY

In the most general sense, the present invention provides a heat not burn consumable comprising a tubular vapour generating member defining a channel therethrough, wherein at least an active portion of the vapour generating member is configured to be heated by a heater to produce vapour, wherein: the tubular vapour generating member has an inlet to the channel at a first end of the consumable, the first end of the consumable being for cooperation with a heating device.

Such a heat not burn consumable may be combined with any one or more features from the following disclosure.

According to a first aspect there is provided a heat not burn consumable comprising: a tubular vapour generating member defining a channel therethrough, wherein at least an active portion of the vapour generating member is configured to be heated by a heater to produce vapour, wherein: the tubular vapour generating member has an inlet to the channel at a first end of the consumable, the first end of the consumable being for cooperation with a heating device; and wherein the active portion of the vapour generating member has a sidewall which has a thickness greater than 0.1 mm.

According to another aspect there is provided a heat not burn consumable comprising a tubular vapour generating member defining a channel therethrough, wherein at least an active portion of the vapour generating member has an internal surface area and is configured to be heated by a heater to produce vapour, wherein: the tubular vapour generating member has an inlet to the channel at a first end of the consumable, the first end of the consumable being for cooperation with a heating device; and wherein the active portion comprises an amount of an active substance which is between 0.0001 milligrams per mm^2 and 0.02 milligrams per mm^2 of said internal surface area.

Conveniently, the overall length of the vapour generating member is greater than 75% or 90% of the total length of the consumable.

Preferably, the overall length of the vapour generating member is substantially equal to the total length of the consumable.

According to another aspect there is provided a heat not burn consumable comprising a tubular vapour generating member defining a channel therethrough, wherein at least an active portion of the vapour generating member is configured to be heated by a heater to produce vapour, and; an inactive structural tube in axial abutment with the tubular vapour generating member and located downstream of the vapour generating member; wherein a wrapper overwraps the vapour generating member and at least a portion of the inactive tube.

Preferably, the active portion has a transverse cross-section substantially equal in size and shape to a transverse cross-section of the inactive tube.

Preferably, the consumable further includes a mixing zone located downstream of the active portion and within the inactive tube.

Advantageously, the consumable has an airflow passage extending between the inlet opening and an outlet opening located at a second end of the consumable, the channel through the active portion forming at least a first portion of the airflow passage, and a channel through the inactive tube forming a second portion.

Conveniently, the sidewall thickness of the active portion is less than 1.5 mm.

Preferably, the active portion has an overall longitudinal length which is greater than 10 mm.

Advantageously, the active portion has an overall longitudinal length which is less than 35 mm.

Conveniently, the channel through the active portion has a transverse cross-section substantially equal in size and shape to a transverse cross-section of the inlet opening.

Preferably, a total mass of an active substrate comprised in the active portion is greater than 100 mg and less than 1000 mg.

Advantageously, the active substrate of the active portion includes between 0.2 milligrams and 2.0 milligrams of active substance.

Conveniently, the active substrate of the active portion includes between 0.0002 milligrams and 0.02 milligrams of active substance per milligram of said active substrate.

Preferably, the consumable has a total longitudinal length less than or equal to 100 mm.

Advantageously, the consumable has a total longitudinal length greater than or equal to 50 mm.

Conveniently, the overall longitudinal length of the channel through the active portion is between 20% and 40% of the total length of the consumable.

Conveniently, the overall longitudinal length through the active passage is between 20% and 40% of the total length of the consumable.

Preferably, further including a mixing zone located downstream of the active portion within the airflow passage.

Advantageously, the consumable further includes a mixing zone located downstream of the active portion within the airflow passage.

Advantageously, the vapour generating member includes an active substance, and wherein the active substance includes nicotine.

Conveniently, the vapour generating member includes a sheet of reconstituted tobacco.

The invention includes the combination of the aspects and preferred features described except where such a combination is clearly impermissible or expressly avoided.

DETAILED DESCRIPTION

Aspects and embodiments of the present invention will now be discussed with reference to the accompanying figures. Further aspects and embodiments will be apparent to those skilled in the art. All documents mentioned in this text are incorporated herein by reference.

In general, the present invention is directed to an HNB consumable. The HNB consumable forms a constituent element of an HNB system. An HNB consumable according to the present invention is configured for use with a heating device. In combination, an HNB consumable and a heating device form an HNB system. The HNB consumable may be configured for engagement with the heating device.

As will be appreciated, the heat not burn (HNB) concepts relies on vaporisation. HNB and HNB devices may therefore be considered vaporisation devices.

Figure 1:
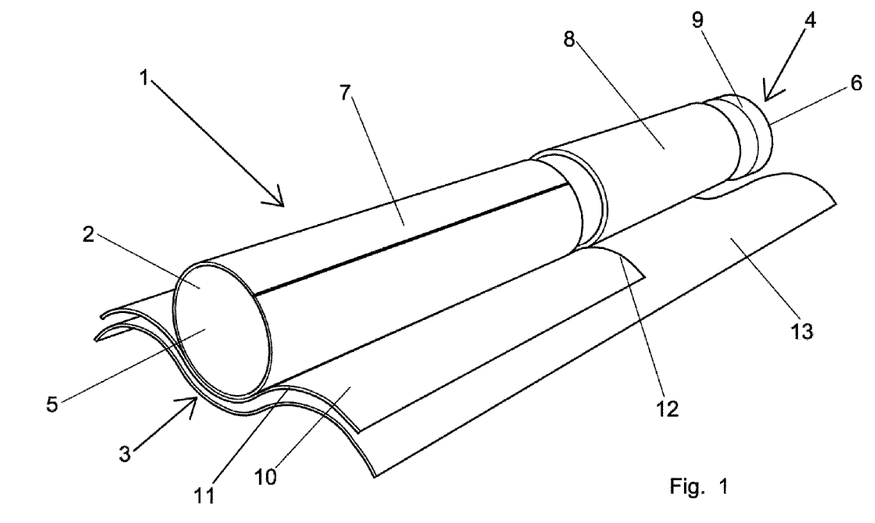
FIG. 1 shows a partially assembled first consumable in accordance with the present invention.

FIG. 1 shows an HNB consumable 1 according to a first embodiment of the invention. The consumable 1 is shown in an opened, part-formed, configuration so that the constituent elements and the relationships between them can be clearly identified. It will be understood that the tipping paper and the overwrap will both be rolled to seal the consumable longitudinally during the manufacturing process.

The consumable 1 has an elongate shape. In other words, the consumable has a longitudinal dimension along a longitudinal axis that is larger than a dimension of the consumable along a transverse axis of the consumable.

The consumable 1 has a generally elongate outer shape. For example, the consumable 1 has an external transverse cross-sectional shape having a generally circular shape. However, the consumable 1 could equally have a different external transverse cross-sectional shape. For example, a generally square, rectangular, or oval shape. The external transverse cross-sectional shape is generally constant along the longitudinal length of the consumable 1.

In a most general sense, the consumable 1 forms an elongate airflow passage 2 which extends from a first end 3 to a second end 4 of the consumable 1. The first end 3 of the consumable 1 may be configured for interaction with a heating device. The second end 4 of the consumable 1 may be configured to form a mouthpiece. The user may directly engage the second end 4 with their mouth, or a mouthpiece component may be attached to the second end, and then, in turn, the user may engage the mouthpiece component. Such a mouthpiece component does not form part of the present invention. As will therefore be appreciated, the first end 3 of the consumable 1 may be considered to represent a so-called "upstream" end of the consumable 1, and the second end 4 of the consumable 1 may be considered to represent a so-called "downstream" end of the consumable 1, in a flow-series sense with respect to the direction of airflow through the consumable 1 along the airflow passage 2 during use.

The consumable has inlet 5 at the first end 3 and an outlet 6 at the second, opposite end 4. In use, the user draws on the second end 4, which causes airflow into the consumable 1 at the inlet 5, through the consumable 1 along the airflow passage 2, to the outlet 6.

Located directly adjacent to the inlet 5, there is a vapour generating member 7 (VGM). The VGM 7 defines a channel therethrough. The channel through the VGM 7 forms a portion of the airflow passage 2 through the consumable 1.

Adjacent to the VGM 7 there is located a supporting structural tube 8. The supporting tube 8 defines a channel therethrough. The channel through the supporting tube 8 forms a portion of the airflow passage 2 through the consumable 1. The supporting tube 8 is located downstream from the VGM 7—i.e. in a flow-series sense, and thus between the VGM 7 and the outlet 6.

The supporting tube 8 may be formed from a paper-based material, for example a cardboard material. The paper-based material of the supporting tube 8 may have a density of greater than 50 g.s.m. (grams per square meter). For example, substantially equal to 100 g.s.m., for example. Thus, the supporting tube 8 is an inactive element insofar as it is configured not to generate a vapour, even if heated.

The supporting tube 8 may define a mixing zone within its central channel. The mixing zone is thus located downstream of the VGM 7. In other words, the mixing zone is located between the VGM 7 and the outlet 6. In the mixing zone, the vapours from the VGM 7 mix with each other, either from the VGM 7, or from other sources. For example, the supporting tube 7 may include perforations through its sidewall. The perforations may allow an airflow into the mixing zone through the perforations.

The supporting tube 8 may also form a cooling zone in the channel therethrough. In the cooling zone, the vapours from the VGM 7 cool, which may result is condensation from vapour to an aerosol for user inhalation.

The channel formed through the VGM 7 may be generally contiguous with the channel through the supporting tube 8. The internal transverse cross sectional shape of the supporting tube 8 may be of the same size and shape as the internal transverse cross-sectional shape of the VGM 7.

Adjacent to, and downstream of, the supporting tube 8 there is located a filter 9. The filter 9 abuts against the downstream end of the supporting tube 8 proximal to the second end 6 of the consumable 1. The filter 9 may alternatively be located within an end of the supporting tube 8 proximal to the second end 6 of the consumable 1. In other words, the filter 9 may be formed within the airflow passage 2 through the consumable 1. The filter 9 is thus located downstream from the VGM 7. Also, the filter 9 is either located downstream from the supporting tube 8 (if the filter 9 abuts the end of the supporting tube 8), or is located downstream from at least a portion of the supporting tube 8 (if the filter 9 is located within the end of the supporting tube 8).

The filter 9 may act as a cooling element, configured to cool a vapour or aerosol passing therethrough. The filter 9 may additionally or alternatively be configured to form an airflow resistance element, which provides a resistance to airflow therethrough. The filter 9 may additionally or alternatively form a filter mixing element within which the vapour from the VGM 7 mixes with other fluid components, either also from the VGM 7, or from other sources. Alternatively, in some embodiments, it is envisaged that the filter 9 may be omitted.

Surrounding the VGM 7 is a tipping paper 10. The tipping paper 10 circumscribes the VGM 7. The tipping paper 10 may be formed from a paper-based material. The paper-based material of the tipping paper 10 may have a density of between 45 and 80 g.s.m., for example. The tipping paper 10 may be held in position surrounding the VGM 7 with an adhesive, for example.

The tipping paper 10 is longer in the longitudinal dimension of the consumable 1 than the VGM 7. Thus, when a first (upstream) longitudinal edge 11 of the tipping paper 10 is aligned with the edge of the inlet 5, then the opposing (downstream) edge 12 of the tipping paper 10 extends beyond the longitudinal extent of the VGM 7, and overlaps with at least a portion of the supporting tube 8. Thus, the tipping paper 10 facilitates the engagement of the VGM 7 with the supporting tube 8. The length of the overlap with the supporting tube 8 may be between 20 and 45 mm, for example.

Including the tipping paper 10 also increases the rigidity and strength of the consumable 1 in the vicinity of the VGM 7.

Surrounding the tipping paper 10, the VGM 7, the supporting tube 8 and the filter 9, is an overwrap 13. The overwrap 13 extends along the full longitudinal length of the consumable 1. The overwrap 13 may be formed from a paper-based material. The paper-based material of the overwrap may have a density of 10 to 30 g.s.m. For example, 15 g.s.m. The overwrap 13 may be held in position surrounding the VGM 7, the supporting tube 8 and the filter 9 with an adhesive, for example.

Figure 2:
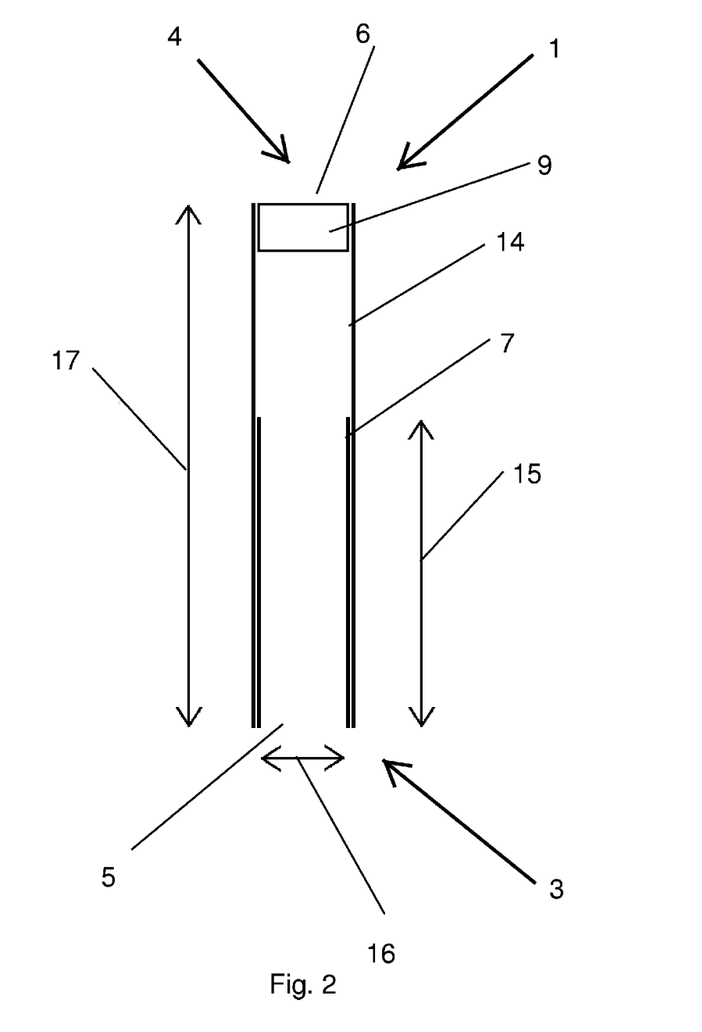
FIG. 2 shows a cross-sectional view through a second consumable in accordance with the present invention.

FIG. 2 shows a longitudinal cross-section through another HNB consumable 1 according to the present invention.

The consumable 1 includes a tubular VGM 7 located generally towards a first end 3 of the consumable 1. At the first end 3 of the consumable 1 is an inlet 5. A filter 9 is located at a second end 4 of the consumable 1, and is formed generally across an outlet 6 of the consumable 1. In this embodiment, the filter 9 is spaced apart from the VGM 7. An external wrapper 14 surrounds and connects the VGM 7 and the filter 9. In the consumable 1 of FIG. 2, the supporting tube 8 and tipping paper 10 are omitted relative to the consumable 1 of FIG. 1; the overwrap of FIG. 1 is replaced by the external wrapper 14 of the consumable 1 of FIG. 2. The external wrapper 14 may be formed from a paper-based material. The paper-based material of the external wrapper 14 may have a density of 20 to 100 g.s.m. The heavier paper of the external wrapper 14, relative to the tipping paper 10, may allow the external wrapper 14 to contribute some rigidity to the consumable 1 of FIG. 2.

Furthermore, by forming the consumable from fewer components, the consumable can be manufactured more simply and at a lower cost.

For the avoidance of doubt, the radial gap between the VGM 7 and the external wrapper 14 is shown for clarity of explanation in FIG. 2. Similarly, the radial gap between the filter 9 and the external wrapper 14 is shown for clarity of explanation. The external wrapper 14 is in contact with an external surface of the VGM 7 and with an external surface of the filter 9.

The VGM 7 has a total longitudinal length 15, L_vgm and an internal diameter 16, D_vgm. The consumable has a total longitudinal length 17, L_cons.

L_vgm/L_cons may be between 0.25 and 0.5. For example between 0.25 and 0.333. Alternatively, 0.50 or greater, 0.55 or greater, 0.60 or greater, 0.65 or greater, 0.70 or greater, 0.75 or greater, 0.80 or greater, 0.85 or greater, 0.90 or greater, or 0.95 or greater. See FIG. 5 for an example.

The consumable 1 may have a total length 17, L_cons, of between 30 mm and 100 mm.

A total length 17, L_cons, may be at least 30 mm, preferably at least 40 mm, more preferably at least 50 mm, more preferably at least 60 mm, more preferably at least 60 mm, more preferably at least 70 mm, more preferably at least 80 mm, more preferably at least 90 mm, A total length 17, L_cons, may be no more than 100 mm, preferably no more than 90 mm, more preferably no more than 80 mm, more preferably no more than 70 mm, more preferably no more than 60 mm, more preferably no more than 50 mm, more preferably no more than 40 mm.

The upper and lower limits for the total length 17, L_cons, of the consumable 1 may be selected independently from the above values, for example a length of between 30 mm and 50 mm; 80 mm and 100 mm.

For example, the consumable 1 may have a total length 17, L_cons, substantially equal to that of that of a traditional cigarette—e.g. 83 mm. Alternatively, the consumable 1 may have a total length 17, L_cons, of between 40 and 60 mm. For example, substantially 50 mm.

The internal diameter 16, D_vgm, of the channel through the VGM 7 may between 3 mm and 12 mm. For example, the internal diameter 16, D_vgm, of the channel through the VGM 7 may be substantially 7.0 mm. The consumable 1 may have an external diameter of a substantially similar diameter range, whilst accounting for additional components located radially outward of the VGM 7 (for example, tipping paper 10 and overwrap 13, or external wrapper 14).

The internal diameter 16, D_vgm, may be at least 3 mm, preferably at least 4 mm, more preferably at least 5 mm, more preferably at least 6 mm, more preferably at least 7 mm, more preferably at least 8 mm, more preferably at least 9 mm, more preferably at least 10 mm, more preferably at least 11 mm.

The internal diameter 16, D_vgm, may be no more than 12 mm, preferably no more than 11 mm, more preferably no more than 10 mm, more preferably no more than 9 mm, more preferably no more than 8 mm, more preferably no more than 7 mm, more preferably no more than 6 mm, more preferably no more than 5 mm, more preferably no more than 4 mm.

The upper and lower limits for the internal diameter 16, D_vgm, may be selected independently from the above values, for example an internal diameter 16, D_vgm, of between 4 mm and 11 mm; 8 mm and 10 mm.

A total radial distance between an internal surface of the VGM 7 to an immediately adjacent external surface of the consumable 1 may be preferably be between 0.5 and 1.5 mm. Preferably between 0.6 and 1.4 mm; preferably between 0.7 and 1.3 m; preferably between 0.6 and 1.2 mm; preferably between 0.9 and 1.1 mm.

A thickness of the VGM 7 may be preferably be between 0.2 and 1.0 mm. Preferably between 0.3 and 0.9; preferably between 0.4 and 0.8 mm; preferably between 0.4 and 0.7 mm; preferably between 0.4 and 0.6 mm; preferably substantially equal to 0.5 mm.

A thickness of the VGM 7 may be at least 0.2 mm, preferably at least 0.3 mm, more preferably at least 0.4 mm, more preferably at least 0.5 mm, more preferably at least 0.6 mm, more preferably at least 0.7 mm, more preferably at least 0.8 mm, more preferably at least 0.9 mm, A thickness of the VGM 7 may be no more than 1.0 mm, preferably no more than 0.9 mm, more preferably no more than 0.8 mm, more preferably no more than 0.7 mm, more preferably no more than 0.6 mm, more preferably no more than 0.5 mm, more preferably no more than 0.4 mm, more preferably no more than 0.2 mm.

The thickness of the VGM 7 may correspond to a thickness of a sidewall of the VGM 7.

The upper and lower limits for the thickness of the VGM 7 may be selected independently from the above values, for example a thickness of between 0.2 mm and 0.8 mm; 0.4 mm and 1.0 mm.

Figure 3:
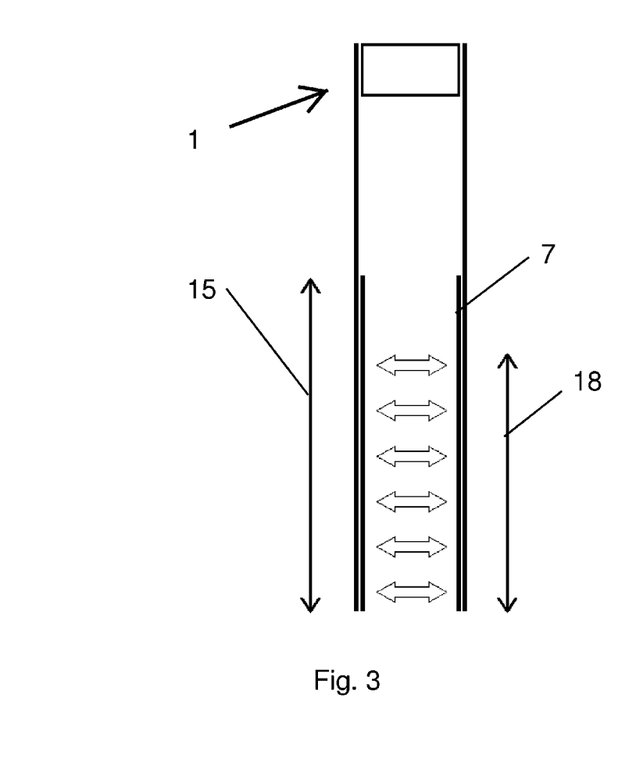
FIG. 3 shows a cross-sectional view through the second consumable in accordance with the present invention and illustrates the principle of internal heating.
Figure 4:
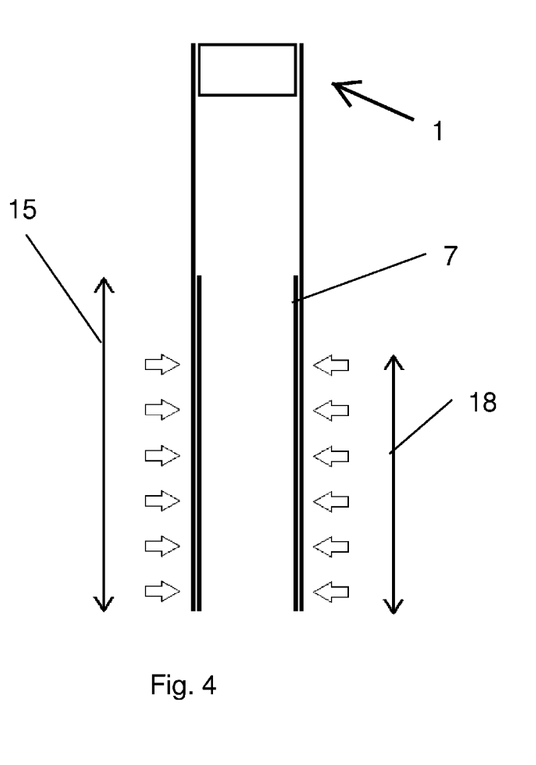
FIG. 4 shows a cross-sectional view through the second consumable in accordance with the present invention and illustrates the principle of external heating.

FIGS. 3 and 4 illustrate the principles of internal and external heating, respectively, of an active portion of the VGM 7 of a consumable 1 according to the present invention.

In FIGS. 3 and 4 the direction of heat application by a heater of a heating device is signified the arrows. The active portion of the VGM 7 may be the portion of the VGM 7 that is configured to be heated by the heating element of the heating device. A particular heating device may be configured to implement internal heating and external heating. The active portion may be longer than a distance along which heat is directly applied to the VGM 7 For example, there may be some heating of the VGM 7 downstream of a region to which heat is directly applied to the VGM 7.

Furthermore, the active portion may comprise the whole of the VGM 7. For example, in the embodiment of FIG. 1, the length of the supporting tube 8 and VGM 7 may be chosen such that the whole of the VGM 7 is comprised in the active portion.

The active portion of the VGM 7 may also include the active substance and/or carrier. Or the active portion may include additional active substance and/or carrier (relative to an inactive downstream portion of the VGM 7).

The active portion of the VGM 7 has an active length 18, L_act. The active length 18, L_act, may be shorter than the total length 17, L_cons of the consumable 1. L_act/L_cons may be between 0.25 and 0.5. Preferably between 0.3 and 0.45; preferably substantially 0.3333 (i.e. ⅓).

The active length 18, L_act, may be shorter than the total length 15, L_vgm of the VGM 7. Alternatively, the active length 18, L_act, may be substantially equal to the total length 15, L_vgm, of the VGM 7.

The active length 18, L_act, may be between 10 and 35 mm, for example.

For all of the embodiments described herein, the channel through the VGM 7 permits the heating of the active portion of the VGM 7 to occur rapidly when heating by a heating device occurs. It is also possible to consistently heat the active portion to a single temperature, or to within a narrow temperature range. This is an improvement on the prior art, where heating of the tobacco is slow and a large temperature range can be formed within the tobacco. For example, some tobacco in the prior art may be burned, while other parts remain sufficiently cool that substantially no aerosol is generated.

A total active internal surface area of the VGM 7 is equal to pi*D_vgm*L_act. This is the total active internal surface area of the VGM 7 that is configured for heating by a heating device with internal heating. For external heating, a total external active surface area of the VGM 7 generally corresponds to the total internal active surface area of the VGM 7.

The skilled person will of course appreciate that the mathematical formula for the internal surface area will be different for a VGM 7 with a different cross sectional shape.

As above, the active internal active surface area of the VGM 7 is equal to pi*D_vgm*L_act. The active internal surface area may be generally equal to the total internal surface area of the VGM 7 when L_vgm is equal to L_act.

A total internal active surface area of the VGM 7 may be at least 100 square millimetres (mm^2), preferably at least 200 mm^2, more preferably at least 300 mm^2, more preferably at least 400 mm^2, more preferably at least 500 mm^2, more preferably at least 600 mm^2, more preferably at least 700 mm^2, more preferably at least 800 mm^2, more preferably at least 900 mm^2, more preferably at least 1000 mm^2; more preferably at least 1100 mm^2, more preferably at least 1200 mm^2, more preferably at least 1300 mm^2, more preferably at least 1400 mm^2, more preferably at least 1500 mm^2, more preferably at least 1600 mm^2, more preferably at least 1700 mm^2, more preferably at least 1800 mm^2, more preferably at least 1900 mm^2.

A total internal active surface area of the VGM 7 may be no more than 2000 square millimetres (mm^2), preferably no more than 1900 mm^2, more preferably no more than 1800 mm^2, more preferably no more than 1700 mm^2, more preferably no more than 1600 mm^2, more preferably no more than 1500 mm^2, more preferably no more than 1400 mm^2, more preferably no more than 1300 mm^2, more preferably no more than 1200 mm^2, more preferably no more than 1100 mm^2, more preferably no more than 1000 mm^2, more preferably no more than 900 mm^2; more preferably no more than 800 mm^2, more preferably no more than 700 mm^2, more preferably no more than 600 mm^2, more preferably no more than 500 mm^2, more preferably no more than 400 mm^2, more preferably no more than 300 mm^2, more preferably no more than 200 mm^2, more preferably no more than 100 mm^2.

The total internal active surface area of the VGM 7 may be selected independently from the above values, for example a total internal active surface area of the VGM 7 of between 300 mm^2 and 1300 mm^2; 500 mm^2 and 600 mm^2.

The VGM 7 comprises a vapour generating substrate. The vapour generating substrate is the component of the VGM 7 in which at least one active substance is located, and from which the active substance may be vapourised. The total mass of the vapour generating substrate in a single consumable may be between 100 and 1000 milligrams (mg).

The total mass of the vapour generating substrate may be at least 100 milligrams, preferably at least 200 milligrams, more preferably at least 300 milligrams, more preferably at least 400 milligrams, more preferably at least 500 milligrams, more preferably at least 600 milligrams, more preferably at least 700 milligrams, more preferably at least 800 milligrams, more preferably at least 900 milligrams.

The total mass of the vapour generating substrate may be no more than 1000 milligrams, preferably no more than 900 milligrams, more preferably no more than 800 milligrams, more preferably no more than 700 milligrams, more preferably no more than 600 milligrams, more preferably no more than 500 milligrams, more preferably no more than 400 milligrams, more preferably no more than 300 milligrams, more preferably no more than 200 milligrams, more preferably no more than 100 milligrams.

The total mass of the vapour generating substrate may be selected independently from the above values, for example total mass of the vapour generating substrate of between 300 milligrams and 900 milligrams; 200 milligrams and 600 milligrams.

A total mass of the vapour generating substrate in the active portion may be selected from the same values as those for the mass of the vapour generating substrate above.

As above, the vapour generating substrate may include at least one active substance. A particular vapour generating substrate may include a total amount of a particular active substance of between 0.2 and 2.0 mg. One such active substance may be nicotine, for example.

A parameterisation of the present invention is the amount of active substance per unit internal active surface area of the VGM 7. For a consumable 1 having 0.2 to 2.0 mg of active substance (e.g. nicotine), and an active portion internal surface of 100 to 2000 mm^2, then the consumable 1 has an active substance surface density of between 0.0001 mg per mm^2 and 0.02 mg per mm^2. Preferably the consumable 1 has an active substance surface density of between 0.0005 mg per mm^2 and 0.015 mg per mm^2; between 0.001 mg per mm^2 and 0.03 mg per mm^2; between 0.0015 mg per mm^2 and 0.025 mg per mm^2.

An example of a VGM 7 according to the present invention is tobacco-based. The VGM 7 may comprise reconstituted tobacco. For example, the VGM 7 may comprise one or more sheets of reconstituted tobacco (see FIGS. 7 to 9, for example). A method for using tobacco material in the preparation of reconstituted tobacco (or "recon") may generally be carried out as follows:

Tobacco in the form of dust, granules, or shredded plant leaf or stem material is first collected (hereinafter "plant material"). The plant material may be a tobacco processing byproduct. The plant material is uniformly admixed with a bonding material which, as the term implies, causes bonding and agglomeration of the plant material. The bonding materials that may be employed in the process include materials that by themselves cause bonding and agglomeration of particles of plant material and also include those materials which indirectly cause such bonding and agglomeration by having the effect of releasing naturally occurring bonding agents contained within the plant material itself which agents subsequently cause the actual bonding and agglomeration of the plant material.

Bonding materials which by themselves cause bonding and agglomeration of the plant material include, for example, film-forming materials, cross-linking agents and the like. Film forming materials and the techniques for converting these materials into water-insoluble fibers, sheets, etc., are well known in the art.

After the plant material has been added to the bonding material, which is present as either a dispersion or solution (or after the plant material is dry mixed with a bonding material and then added to a solvent), the resulting mixture is then thoroughly blended so as to form a uniform, homogeneous mixture. This mixture is then treated by one of many methods known in the art in order to either insolubilize the film forming material added to or released from the plant material or allowed to cross-link if a cross-linking agent has been added.

It is to be understood that the resulting bonded plant material may be produced in a wide ranges of shapes and configurations of varying dimensions. Thus, as noted above, the mixture of the bonding material and tobacco dust may be spun into fibres, rolled into sheets, cast in a frame, or extruded into other shapes.

Preferably plant material by-products, such as stems, fines, etc., are mixed with water to form a slurry and then refined. After adding the agglomerated particles of plant material to the slurry, the slurry is thereafter mixed by techniques conventional in the art such that a thorough blending of the components takes place to form a uniform homogeneous mixture. A reconstituted plant material sheet is formed from the slurry either by a paper-making process, by forming the slurry into a layer on a paper substrate, by casting the slurry in a mould, or by extrusion.

The preparation of reconstituted plant material by means of a paper-making process is well known in the art as exemplified by Canadian Pat. No. 862,497 which has been incorporated herein by reference. The processes therein described are particularly advantageous with the paper-making process for preparing reconstituted tobacco material ("recon") sheets.

Generally, after a sheet of material containing the agglomerated particles of plant material has been formed by means of the papermaking process, it is then dried and cut or pressed into the desired physical form.

As referred to herein, the VGM 7 may include, or be formed from, a plant product. The "Plant Product": denotes a plant from which an active substance may be aerosolized into a breathable fluid stream for inhalation by a user. For the avoidance of doubt, suitable plant products include *Amaranthus dubius, Arctostaphylos uva-ursi* (Bearberry), *Argemone mexicana, Arnica, Artemisia vulgaris, Yellow Tees, Galea zacatechichi, Canavalia maritima* (Baybean), *Cannabis, Cecropia mexicana* (Guamura), *Cestrum noctumum, Cynoglossum virginianum* (wild comfrey), *Cytisus scoparius, Dam iana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia inflata, Lobelia siphilitica, Nepeta cataria* (Catnip), *Nicotiana* species (Tobacco), *Nymphaea alba* (White Lily), *Nymphaea caerulea* (Blue Lily), *Opium poppy, Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (Damiana), *Verbascum* (Mullein), *Zamia latifolia* (Maconha Brava) together with any combinations, functional equivalents to, and/or synthetic alternatives of the foregoing.

As referred to herein, the "Active Substance" denotes a chemical and/or physiologically active species, or combination or mixture of such chemical and/or physiologically species, that are intended to be aerosolized, and that may provide the user with a recreational and/or medicinal effect when a breathable fluid stream comprising the aerosol is inhaled by a user. For the avoidance of doubt, suitable chemical and/or physiologically active species includes the group consisting of: nicotine, cocaine, THC, CBD, caffeine, cannaboids, opiates and opioids, cathine and cathinone, kavalactones, mysticin, beta-carboline alkaloids, salvinorin A together with any combinations, functional equivalents to, and/or synthetic alternatives of the foregoing.

The remaining figures show further consumables 1 and principles according to the present invention, and are described below. The above considerations in respect of the embodiments of FIGS. 1 and 2 apply equally to the embodiments of the remaining figures. The following considerations in respect of the remaining figures apply equally to the embodiments of FIGS. 1 and 2.

FIG. 5 shows another consumable 1 according to the present invention. The consumable 1 includes a tubular VGM 7. The VGM 7 extends substantially between a first (upstream) end 3 and a second (downstream) end 4 of the consumable 1. The VGM 7 is sufficiently rigid to support its own weight without collapse. For example, the VGM 7 may be formed from a sheet member of reconstituted tobacco (see FIGS. 7 to 9, for example). The sheet member may have a density of between 80 g.s.m. and 145 g.s.m.

At the first end 3 is an inlet 5. A filter 9 is located at the second end 4 of the consumable 1, and is formed across an outlet 6 of the consumable 1. An external wrapper 19 surrounds and interconnects the VGM 7 and the filter 9. In the consumable 1 of FIG. 5, the supporting tube 8, tipping paper 10, and overwrap 13 are omitted relative to the consumable 1 of FIG. 1.

The filter 9 may be located to abut an end of the VGM 7 located adjacent the second end 4 of the consumable 1, or the filter 9 may be located within the VGM 7 located adjacent the second end 4 of the consumable 1.

The external wrapper 19 may be formed from a paper-based material. The paper-based material of the external wrapper 19 may have a density of 20 to 100 g.s.m.

The external wrapper 19 may be omitted. Additionally or alternatively, the filter 9 may be omitted. If the VGM 7 is of sufficient rigidity, the consumable 1 may consist substantially of the VGM 7 only. For the avoidance of doubt, a filter 9 may be included within an end of such a VGM 7. Again, reducing the number of components in the consumable 1 in this manner may allow for the consumable 1 to be simpler and more cost effective to manufacture.

Figure 5:
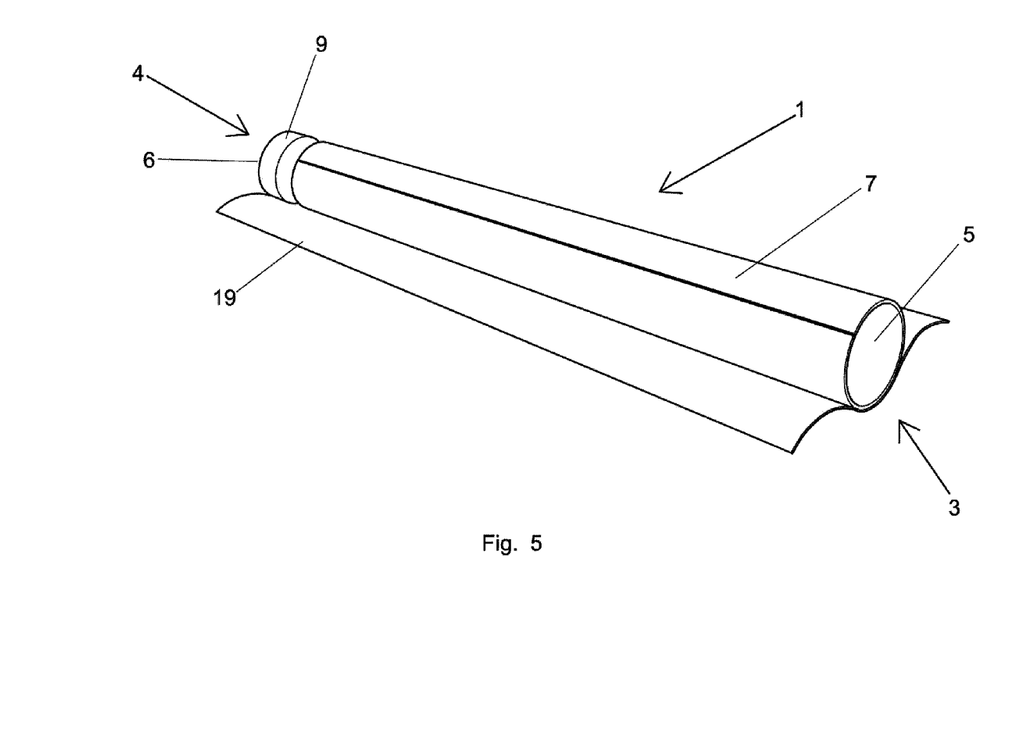
FIG. 5 shows a partially assembled third consumable in accordance with the present invention.
Figure 6:
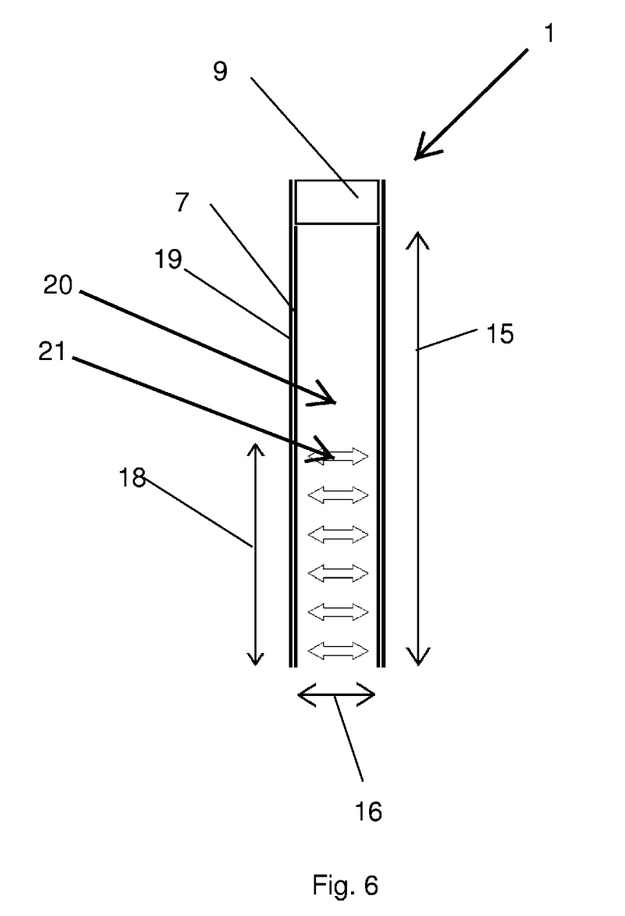
FIG. 6 shows a cross-sectional view through the third consumable in accordance with the present invention.

FIG. 6 shows a longitudinal cross-section through the consumable 1 according to the present invention shown in FIG. 5. The VGM 7 has an active portion having an active length 18, L_act. The total length 15, L_vgm of the VGM 7 is also shown. Internal heating of the active portion of the VGM 7 is represented by the double headed arrows. The external wrapper 19 is shown wrapping the VGM 7 and the filter 9.

In FIG. 6, the radial gap between the VGM 7 and the external wrapper 19 is shown for clarity of explanation only. Similarly, the radial gap between the filter 9 and the external wrapper 19 is shown for clarity of explanation only. The external wrapper 19 is in contact with an external surface of the VGM 7 and with an external surface of the filter 9.

In the embodiment of FIGS. 5 and 6, the ratio of the total length 15 of the VGM 7, L_vgm, to the total length, L_cons, of the consumable 1, L_vgm/L_cons may be greater than or equal to 0.5, preferably greater than or equal to 0.55, preferably greater than or equal to 0.6, preferably greater than or equal to 0.65, preferably greater than or equal to 0.7, preferably greater than or equal to 0.75, preferably greater than or equal to 0.8, preferably greater than or equal to 0.85, preferably greater than or equal to 0.9, preferably greater than or equal to 0.95.

The active length, L_act, 18 of the active portion of the VGM 7 may be an active fraction of the total length 15, L_vgm, of the VGM 7. In other words, L_act/L_vgm may be equal to or less than 1.

This leaves an inactive portion 20 of the VGM 7 located downstream of the active portion 21. The inactive portion 20 is similar to the inactive supporting tube 8 of the embodiment illustrated in FIG. 1. The inactive portion 20 may form a mixing zone in the channel therethrough. In the mixing zone, the vapour from the VGM 7 mixes with other fluid components, either from the VGM 7, or from other sources (e.g. perforations formed in the VGM 7). The inactive portion 20 may also form a cooling zone in the channel therethrough. In the cooling zone, the vapour from the VGM 7 cools, which may result in condensation from vapour to aerosol.

Figure 7:
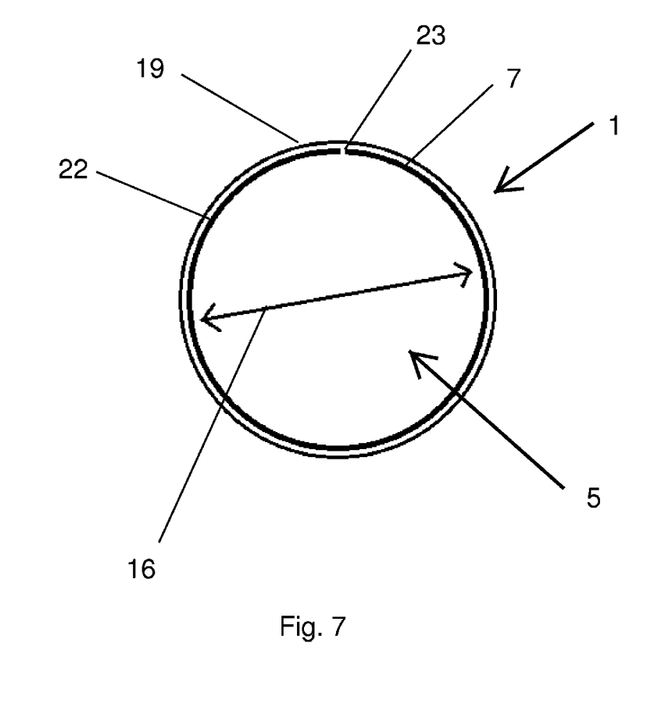
FIG. 7 shows an end view of a consumable in accordance with the present invention.

FIG. 7 shows an end view of a consumable 1 according to the present invention. The consumable 1 includes a VGM 7 and an external wrapper 19. An intervening tipping paper is not present in the consumable 1 of FIG. 7, but could nevertheless be included between the VGM 7 and the external wrapper 19. Thus the configuration of the VGM 7 of FIG. 7 is applicable to the consumables of any preceding Figures.

The VGM 7 is formed from a sheet member 22 (this is also an option for the consumables of FIGS. 1 to 6). The sheet member 22 is formed into the tubular VGM 7 by rolling exactly once. That is, two opposing edges of the sheet member 22 are brought into mutual abutment along a longitudinal seam 23 of the sheet member 22. In other words, there is no mutual overlap between two opposing portions of the sheet member 22. The two opposing edges of the sheet member 22 that are brought into mutual abutment may not be attached to one another; they may simply be retained in abutment so that the VGM 7 has the tubular shape. The two opposing edges may be retained in abutment by the external wrapper 19, or by virtue of the rigidity of the sheet member 22.

In FIG. 7, an inlet 5 of the tube consumable 1 is apparent. The size and shape of the inlet 5 is defined by the internal surface of the VGM 7. The internal diameter 16 of the VGM 7 is indicated in FIG. 7.

Figure 8:
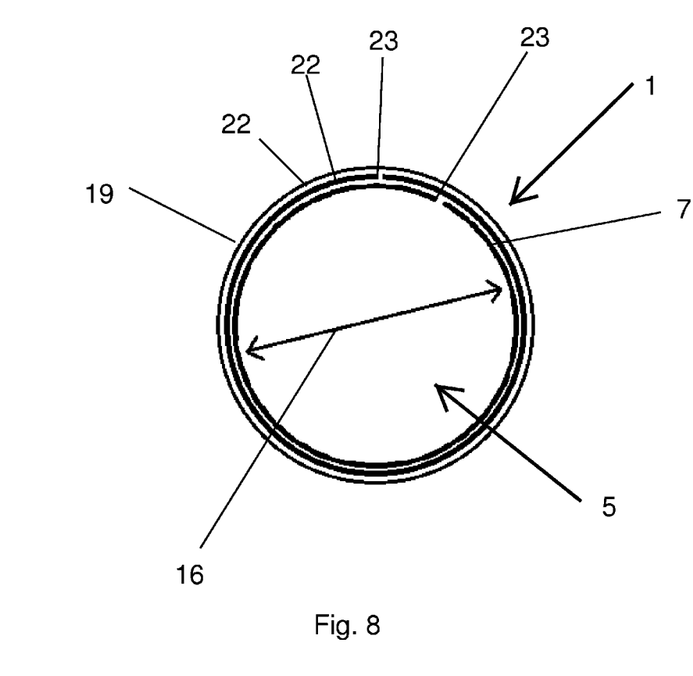
FIG. 8 shows an end view of an alternative consumable in accordance with the present invention.

FIG. 8 shows an end view of another consumable 1 according to the present invention. The consumable 1 of FIG. 8 is similar to the consumable of FIG. 7, and similar elements are labelled with the same reference numerals. The VGM 7 of the consumable of FIG. 8 includes two generally concentric sheet members 22. Each sheet member 22 has two opposing edges in mutual abutment at a respective longitudinal seam 23. The positions of the two longitudinal seams 23 have an angular offset between each other. In other words, the two longitudinal seams 23 are not aligned with one another. This may improve the rigidity of the VGM 7 and the consumable 1.

The VGM 7 may include more than the two sheet members 22 of FIG. 8. The longitudinal seams 23 of the sheet members 22 may each have an angular offset from one another. Alternatively, all directly adjacent pairs of sheet members 22 may have an angular offset between the positions of the respective pair of longitudinal seams 23.

Figure 9:
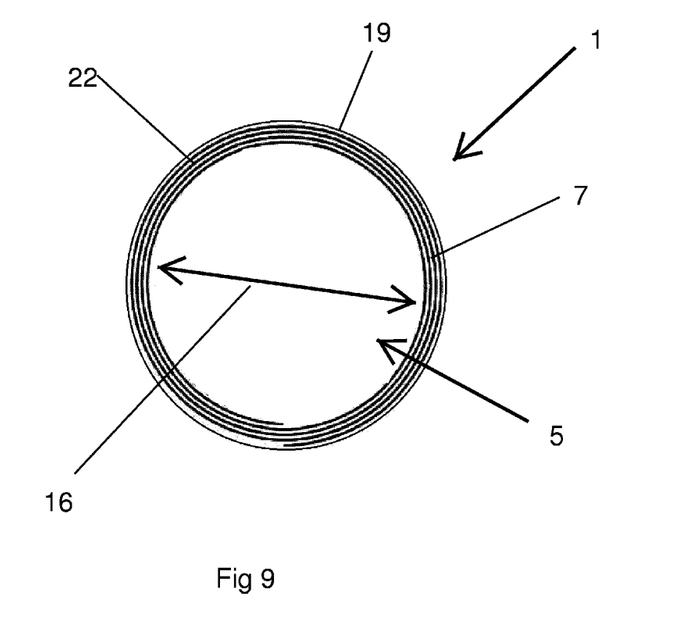
FIG. 9 shows an end view of another alternative consumable in accordance with the present invention.

FIG. 9 shows an end view of a consumable 1 according to the present invention. The consumable 1 includes a VGM 7 and an external wrapper 19. An intervening tipping paper 10 is not present in the consumable 1 of FIG. 9, but could nevertheless be included between the VGM 7 and the external wrapper 19.

In the consumable of FIG. 9, the VGM 7 is formed from a sheet member 22. The sheet member 22 is formed into a tubular VGM 7 by rolling more than once. In other words, there is a mutual overlap between two opposing portions of the sheet member 22. In FIG. 9, the sheet member 22 is shown overlapping exactly 3 times. By overlapping an integer number of times, a more uniform thickness of a wall of the VGM 7 may be achievable. The rolled sheet member 22 may be retained in the rolled configuration by the external wrapper 19, or by virtue of the material of the VGM 7. For example, the sheet member 22 may be configured to have rigidity properties that means that the sheet member remains substantially in the rolled configuration. Alternatively, the sheet member 22 may be held in the rolled configuration by an adhesive. The sheet member 22 may overlap less than 3 times or more than 3 times. The sheet member 22 may overlap up to 5 times.

The sheet member 22 may be spiral rolled. Spiral rolling may allow for a greater overlapping surface area for adhesive application, for example.

In FIG. 9, an inlet 5 of the tube consumable 1 is apparent. The size and shape of the inlet 5 is defined by the internal surface of the VGM 7. The internal diameter 16 of the VGM 7 is indicated in FIG. 9.

In any of the above-described embodiments, the VGM 7 may be formed from a sheet member 22 of reconstituted tobacco having a density between 80 and 145 g.s.m., for example. If an overlapping configuration is used (e.g. FIG. 9) or a configuration with multiple layers (e.g. FIG. 8), then the density of the sheet member may be lower.

Thus the configurations of the VGM 7 illustrated in FIGS. 7 to 9 are all applicable to any consumable according to the present invention.

Each of the above-described embodiments may be configured to output a "puff of aerosol when drawn upon by a user. As will be appreciated by those skilled in the art, a puff is a single draw by user into the mouth, which may then be inhaled. The smoking of a traditional cigarette generally includes taking a plurality of puffs, for example, 10 puffs.

The carrier is vapourised from the active portion of the VGM 7 The active substance is also vapourised from the VGM 7. Both are entrained in an airflow from the inlet 5. Both the carrier and active substance vapours form an aerosol for inhalation by the user via the outlet 6. The aerosol includes the active substance and the carrier.

The carrier may be polyglycol (PG), vegetable glycerine (VG) or polyethylene glycol (PEG), or any combination thereof, for example.

In use, a user draws on the outlet 6 of the consumable 1 (for example) to take a single puff of aerosol into the user's mouth, which may then be inhaled. The person skilled in the art will appreciate that there are clearly differences in the puffs taken by different users (due to physiological differences or user preference, for example), A puff may be output from the device when a user draws on a device for between 0.5 and 5.0 seconds, for example. The puff may have a volume of between 20 and 120 millilitres (ml). For example, 50 to 60 ml. The puff may be output during a period when the VGM 7 is heated by a heater having an activation temperature. The activation temperature may between 170 degrees Celsius and 250 degrees Celsius. The heater may be maintained at substantially the activation temperature throughout the user's draw.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

We claim:

1. A heat not burn consumable comprising:
    a tubular vapour generating member defining a channel therethrough, wherein at least an active portion of the vapour generating member includes an aerosol former and is configured to be heated by a heater to produce vapour without burning the aerosol former, wherein:
    the tubular vapour generating member has an inlet to the channel at an open first end of the consumable, the open first end of the consumable configured for cooperation with a heating device;
    a supporting structural tube in axial abutment with the tubular vapour generating member downstream of the vapour generating member, wherein the structural supporting tube is an inactive element;
    a wrapper overwrapping the vapour generating member and at least a portion of the supporting structural tube;
    a filter downstream of at least a portion of the supporting structural tube; and
    a hollow open space within the supporting structural tube between the active portion and the filter, the hollow open space providing a mixing zone.

2. The heat not burn consumable of claim 1 wherein the consumable has an airflow passage extending between the inlet and an outlet opening located at a second end of the consumable, the channel through the active portion forming at least a portion of the airflow passage.

3. The heat not burn consumable of claim 1 wherein the active portion of the vapour generating member has a sidewall which has a thickness between 0.2 and 1.0 mm.

4. The heat not burn consumable of claim 1 wherein the entire consumable has a constant external diameter.

5. The heat not burn consumable of claim 1, wherein the channel through the active portion has a transverse cross-section substantially equal in size and shape to a transverse cross-section of the inlet opening.

6. The heat not burn consumable of claim 1 wherein the filter is at a second end of the consumable, opposite from the open first end, and the channel extends from the open first end to the filter, with the channel having a constant inside diameter.

7. The heat not burn consumable of claim 1 wherein a total mass of an active substrate in the active portion is greater than 100 mg and less than 1000 mg.

8. The heat not burn consumable of claim 7 wherein the active substrate of the active portion includes between 0.2 milligrams and 2.0 milligrams of active substance.

9. The heat not burn consumable of claim 7 wherein the active substrate of the active portion includes between 0.0002 milligrams and 0.02 milligrams of active substance per milligram of said active substrate.

10. The heat not burn consumable of claim 1 wherein the vapour generating member is configured to be heated by a heater inserted into the consumable through the open first end of the consumable.

11. The heat not burn consumable of claim 1 having a total longitudinal length greater than or equal to 50 mm.

12. The heat not burn consumable of claim 1 wherein the vapour generating member includes an active substance, wherein the active substance includes nicotine.

13. The heat not burn consumable of claim 1 wherein the vapour generating member includes a sheet of reconstituted tobacco.

14. The heat not burn consumable of claim 1 wherein the entire consumable has only a single filter, and the single filter is at a downstream end of the entire structural tube, at a second end of the consumable.

15. The heat not burn consumable of claim 1 wherein structural tube comprises a material impervious to vapor.

16. The heat not burn consumable of claim 1 wherein the structural tube is free of perforations.

17. The heat not burn consumable of claim 1 wherein the consumable is cylindrical and is configured for cooperation with a heating device which radially heats the tubular vapour generating member.

18. The heat not burn consumable of claim 1 wherein the consumable is configured to be inserted into a heater device.

19. The heat not burn consumable of claim 1 wherein the channel extends unobstructed from an inlet opening entirely through the consumable to the filter.

20. A heat not burn consumable comprising:
a tubular vapour generating member defining a channel therethrough, wherein at least an active portion of the vapour generating member includes an aerosol former and has an internal surface area configured to produce vapour when heated by a heater, wherein:
the tubular vapour generating member has an inlet to the channel at an open first end of the consumable, the open first end of the consumable configured for cooperation with a heating device;
the channel having a transverse cross-section substantially equal in size and shape to a transverse cross-section of the inlet opening;
a supporting structural tube, downstream of the active portion; and
perforations through a sidewall of the supporting structural tube which allow air flow into a mixing zone within the supporting structural tube.

21. The heat not burn consumable of claim 20 wherein an amount of an active substance of the active portion is between 0.0001 milligrams per $mm^2$ and 0.02 milligrams per $mm^2$ of the internal surface area.

22. The heat not burn consumable of claim 20 wherein the active portion has a sidewall which has a thickness between 0.2 and 1.0 mm.

23. A heat not burn consumable, comprising:
a tubular vapor generator having an open upstream end configured for engagement with a heating device;
the vapor generator having an active portion containing an aerosol former configured to be heated by the heating device to produce vapor without burning the aerosol former;
a structural tube having an upstream end in axial abutment with a downstream end of the tubular vapor generator;
a wrapper overwrapping at least parts of the tubular vapor generator and the structural tube;
a filter at a downstream end of the structural tube; and
a channel extending from the open upstream end of the tubular vapor generator to the filter, the channel having a constant inside diameter, and the channel including a hollow empty open space in the structural tube between the active portion and the filter, the hollow empty open space providing a mixing zone.

24. The heat not burn consumable of claim 23 wherein the entire consumable has
a constant outside diameter, and a single filter at a second end of the consumable.

* * * * *